United States Patent

Keller

[11] Patent Number: 6,132,467
[45] Date of Patent: Oct. 17, 2000

[54] ENDOPROSTHESIS, IN PARTICULAR FOR THE STERNOCLAVICULAR JOINT

[75] Inventor: Arnold Keller, Kayhude, Germany

[73] Assignee: Waldemar Link (GmbH & Co.), Hamburg, Germany

[21] Appl. No.: 08/631,515

[22] Filed: Apr. 12, 1996

[30] Foreign Application Priority Data

Apr. 13, 1995 [DE] Germany .................. 295 06 419 U

[51] Int. Cl.$^7$ .................................................. A61F 2/30
[52] U.S. Cl. ............................................................. 623/18.11
[58] Field of Search ................................. 623/16, 18, 19, 623/20, 21, 22, 23, 21.11, 21.12, 21.13–21.19, 18.11, 18.12, 16.11

[56] References Cited

U.S. PATENT DOCUMENTS

| | | | |
|---|---|---|---|
| 3,694,821 | 10/1972 | Moritz | 623/20 |
| 3,795,922 | 3/1974 | Herbert et al. | 623/20 |
| 3,815,157 | 6/1974 | Skorecki . | |
| 3,818,512 | 6/1974 | Shersher | 623/22 |
| 3,837,008 | 9/1974 | Bahler et al. | 623/21 |
| 3,916,451 | 11/1975 | Buechel et al. | 623/22 |
| 3,978,528 | 9/1976 | Crep | 623/19 |
| 3,990,118 | 11/1976 | Strickland | 623/18 |
| 4,106,128 | 8/1978 | Greenwald . | |
| 4,538,305 | 9/1985 | Engelbrecht et al. | 623/18 |
| 4,655,778 | 4/1987 | Koeneman | 623/18 |
| 4,770,658 | 9/1988 | Geremakis | 623/22 |
| 4,770,661 | 9/1988 | Oh | 623/22 |
| 4,892,545 | 1/1990 | Day . | |
| 5,133,761 | 7/1992 | Krouskop | 623/21 |
| 5,628,740 | 5/1997 | Mullane | 606/61 |
| 5,984,971 | 11/1999 | Faccioli et al. | 623/21 |

FOREIGN PATENT DOCUMENTS

| | | |
|---|---|---|
| 0 214 773 | 3/1987 | European Pat. Off. . |
| 0 502 815 | 9/1992 | European Pat. Off. . |
| 2 558 721 | 8/1985 | France . |
| 2 045 085 | 10/1980 | United Kingdom . |

*Primary Examiner*—V. Milliw
*Assistant Examiner*—Alvin Stewart
*Attorney, Agent, or Firm*—Morrison & Foerster, LLP

[57] ABSTRACT

The present invention provides an endoprosthesis for a joint between two bones which cannot be distracted, or which can be distracted only with difficulty. A suitable joint for the endoprosthesis is the sternoclavicular joint. The endoprosthesis has two components, one of which may be attached to the collar bone, and the other which may be attached to the breastbone. One component has a joint head which is insertable into the enclosure part of the second component. The joint head on one component is introduced from the side of the enclosure part on the second component by means of a lateral installation opening in the enclosure part. This arrangement allows little or no distraction of the bones to which the endoprosthesis components are attached when the components are connected.

20 Claims, 2 Drawing Sheets

Fig. 1
Fig. 2
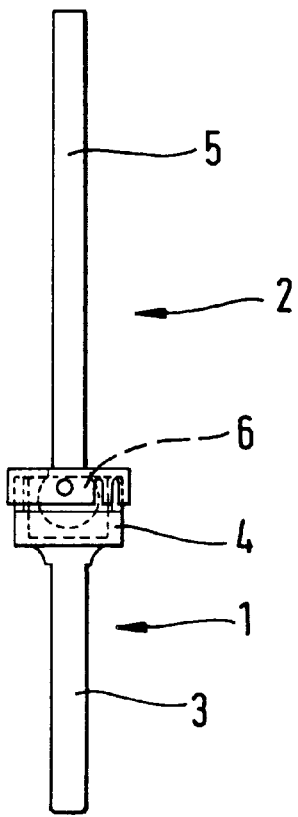
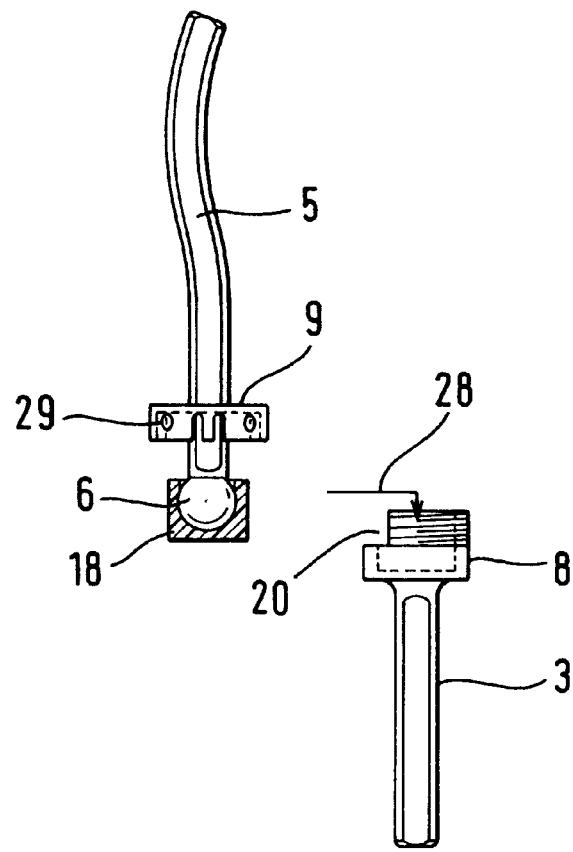

ENDOPROSTHESIS, IN PARTICULAR FOR THE STERNOCLAVICULAR JOINT

BACKGROUND OF THE INVENTION

The collarbone (clavicle) and the breastbone (sternum) are connected to each other by a cartilaginous joint which, when damaged, causes discomfort. One might consider replacing the joint by a prosthesis, but known types of prostheses are not suitable for this purpose, since their implantation generally requires distraction of the bones which are to be connected by the prosthesis. However, the collarbone and the breastbone can be distracted only with difficulty.

SUMMARY OF THE INVENTION

The present invention provides an endoprosthesis for replacing a joint between bones which cannot be distracted, or which can be distracted only with difficulty. In particular, an endoprosthesis for the sternoclavicular joint is contemplated by the present invention.

One embodiment of the present invention provides an Endoprosthesis for a joint between two bones which cannot be distracted, or which can be distracted only with difficulty (e.g. the sternoclavicular joint). In this embodiment, the endoprosthesis has two prosthesis components (1, 2) which each have a fastening part (3, 5) for fastening on the associated bone and which form a joint which consists of a joint head (6) which is connected to the first (5) of the two fastening parts via a neck part (17), and of an enclosure part (4) which is connected to the second fastening part (3), which receives the joint head (6) with pivoting movement, and has a neck opening (16), directed away from the fastening part (17). This embodiment is characterized in that the enclosure part (4) has an installation opening (20) arranged laterally in relation to the neck opening (16).

The present invention contemplates a prosthesis with two components connected to form a universal type joint which can be pivoted in all directions like a ball-and-socket joint. In one embodiment, one component of the prosthesis comprises a joint head which is enclosed in a pivotable manner by an enclosure part arranged on the second component. This mode of construction is known per se in the prosthetic arts (U.S. Pat. No. 4,106,128; FR-A 2,558,721; GB-A 2,045,085; U.S. Pat. No. 3,815,157; EP-A 214,773). This mode of construction, however, means that after the prosthesis components have each been inserted into their associated bones, these bones have to be distracted so that the joint head can be inserted into the enclosure part. This is unsatisfactory since the collarbone and the breastbone can be distracted only with difficulty. The present invention, however, contemplates that the joint head be introduced into the enclosure part from the side through a lateral installation opening in the enclosure part.

In one embodiment, the present invention contemplates two prosthesis components each having a fastening means by which they are fastened on the associated bone. In one embodiment, these are shaft-like parts, as are known per se. In one embodiment, the enclosure part encloses the joint head by at least 180° (preferably more than 180°) in order to form a secure pivot seat for the joint head. In one embodiment, the enclosure part has a neck opening through which is guided the neck connecting the head to the associated fastening part. In one embodiment, the fastening part is shaft-shaped, and the neck part is that area of the shaft next to the head (i.e. the neck part is a part of the shaft).

The present invention also contemplates a method employing the prosthesis of the present invention. In one embodiment the two prosthesis components of the present invention are first connected to the associated bones while they are mutually offset in relation to their natural line of connection. The two prosthesis components are then connected to each other by means of the head of one component being introduced through the lateral installation opening into the enclosure part of the second component. In one embodiment a closing part is provided to close off the installation opening so that the head cannot escape from the enclosure part.

A variety of enclosure part configurations are contemplated. In one embodiment, the enclosure part is formed by a pot-shaped part which is connected to the associated fastening part and whose side wall is open so as to form the installation opening.

In one embodiment, the present invention contemplates a closing part which forms a ring that can be connected to the side wall of the pot-shaped part and which can be connected to said pot-shaped part by means of a thread, a bayonet catch, a snap-on catch or the like.

In one embodiment, in order to avoid metal-to-metal contact between the joint head and the enclosure part, a slide collar is provided between these parts. In one embodiment, the slide collar is made of a material which promotes sliding, such as polyethylene. In a further embodiment, the slide collar is designed such that it is closed all around its side, the width of the installation opening of the enclosure part corresponding at least to the external diameter of the slide collar. This has the advantage that the slide collar can be fitted on the head before the prosthesis components are brought together, and the head can be inserted into the enclosure part together with the slide collar.

In another embodiment, the slide collar has an opening constriction which can be passed through by the joint head with elastic expansion of the slide collar. In this embodiment, the outside of the slide collar is supported by the enclosure part in such a way that the slide collar cannot expand and preventing the joint head from escaping from the slide collar in the installed state. Tensile forces can also be transmitted by the prosthesis in this way. In a further embodiment, the diameter of the neck opening, in the annularly shaped closing part, may be greater than the external diameter of the joint head, since only the slide collar need be held secure by the closing part.

In one embodiment, the joint head is spherical so that the sliding movement of its surface in relation to the slide collar makes possible the movement of the joint. In one embodiment, the joint head has a flange plate at the end of the neck part, which flange plate is surrounded by an elastic bed within the enclosure part. In this manner the joint movement is made possible by deformation of the elastic bed. In this embodiment the joint head need not be circular and can be surrounded by a collar forming the elastic bed.

BRIEF DESCRIPTION OF THE DRAWINGS

The invention is explained in greater detail hereinbelow with reference to the drawing which represents certain preferred embodiments, wherein:

FIG. 1 is a side view of the prosthesis, to approximately natural scale,

FIG. 2 shows the prosthesis during fitting,

DESCRIPTION OF THE PREFERRED EMBODIMENTS

Figure 5:
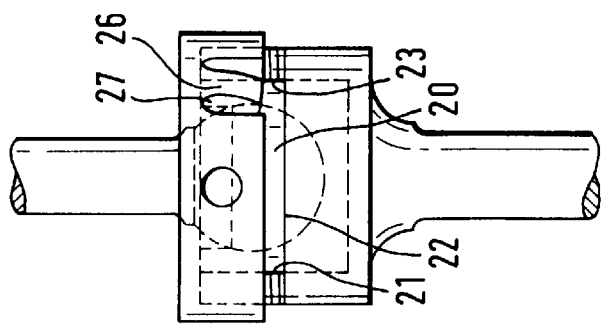
FIGS. 4 and 5 show a longitudinal section and a side view, respectively, on a larger scale.
Figure 4:
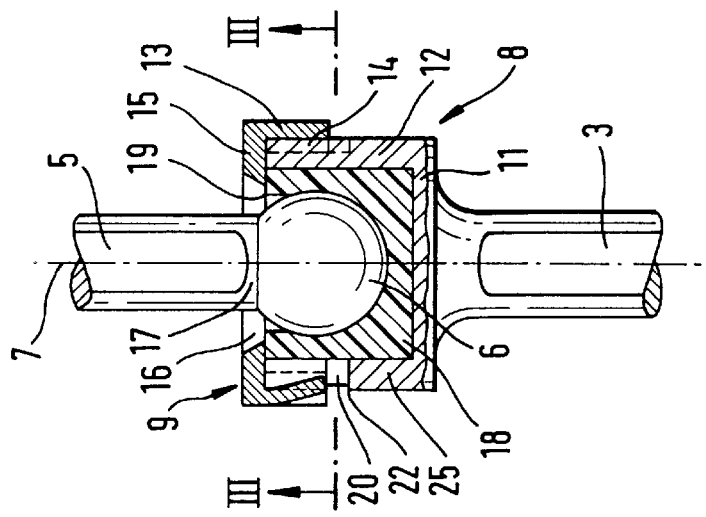
Figure 3:
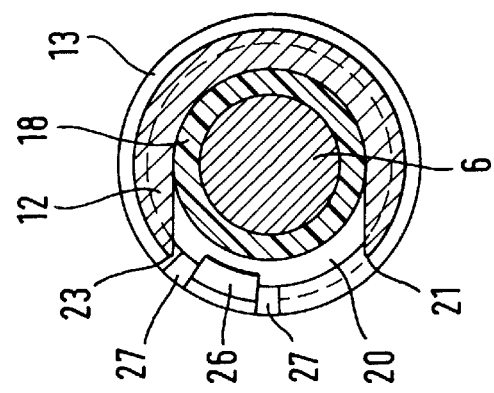
FIG. 3 is a cross-section along the line III—III in FIG. 4, on a larger scale.

The invention is described with reference to a sternoclavicular joint prosthesis illustrated in FIGS. 1–5. In this regard, a sternal component 1, which is to be connected to the breastbone, and the clavicular component 2, which is to be connected to the collarbone. The shaft 3 of the sternal component 1 forms its fastening part and is connected firmly to an enclosure part 4, while the shaft 5, which forms the fastening part of the clavicular part of the prosthesis, is connected to a spherical joint head 6 which is received by the enclosure part 4. The two prosthesis components can be pivoted in all directions relative to each other, about the midpoint of the joint head 6 and of the enclosure part 4, and can additionally be rotated about the common longitudinal axis. They can transmit pressure forces and moderate tensile forces in the longitudinal direction. The expression 'longitudinal direction' refers in this context to the axis defined by the longitudinal axis 7 of the enclosure part 4. The expression 'lateral' refers to directions which lie lateral or transverse to this axis 7.

The fastening parts 3, and 5 of the two prosthesis components are in the form of shafts which can also be curved in a suitable manner. However, the fastening parts can also be of a different configuration.

The enclosure part 4 is made up of a pot-shaped part 8 and a closing ring 9. The pot-shaped part 8 has a base 11, which is connected integrally to the shaft 3, and also a side wall 12. The closing ring 9 has a cylindrical part 13 which can be connected via a thread 14 to the wall 12 of the pot-shaped part 8, and a flange part 15 which forms an opening 16. The latter is referred to as the neck opening because it constitutes the passage for a neck 17 which is provided between the joint head 6 and the fastening part 5. The neck lies in the area of the neck opening 16 and has a smaller diameter than the latter in order to permit a pivoting movement of the prosthesis component 2. In FIGS. 1–5, the neck part 17 is formed by that area of the shaft-shaped fastening part 5 lying adjacent to the joint head 6, but does not differ in cross-section from this fastening part 5.

The joint head 6 sits in a slide collar 18 made of polyethylene and designed in the shape of a small pot. Its outer shape matches cylindrically the internal diameter and the internal length of the enclosure part formed by 8 and 9. The cavity of the slide collar 18 (seen in longitudinal section) is designed spherically through more than 1800. Its free opening 19 has an internal diameter which is smaller than the diameter of the joint head 6. By virtue of the resilience of the material of the slide collar 18, it can be snapped onto the joint head 6, as long as it is not yet enclosed by the enclosure part 8. However, if the enclosure part is tightly surrounding the slide collar 18, it prevents the latter from elastically expanding, with the result that the joint head 6 is held secure in the slide collar even in the event of tensile forces acting in the longitudinal direction. The internal diameter of the neck opening 16 of the closing ring 9 is slightly smaller than the external diameter of the slide collar 18, so that the latter is held secure in the enclosure part. However, the neck opening 16 can be larger than the external diameter of the joint head 6.

The side wall 12 of the pot-shaped part 8 of the enclosure part 4 has a lateral opening 20 which is delimited by the edges 21, 22, 23. This opening 20 does not extend over the entire length of the side wall 12 as far as the base part 11, but instead over only a part thereof, so that a wall part 25 remains in the area of the opening 20. The slide collar 18 is therefore enclosed all round by the wall 12, 25, even on that side on which the opening 20 is located, and is thus held secure as long as the flange 15 of the closing ring 9 prevents it from moving in the longitudinal direction to the extent that its bottom edge reaches the opening edge 22.

The cylindrical part 13 of the closing ring 9 includes a securing tongue 26 which is formed by two axially parallel incisions 27 and is positioned over the opening 20 in the installed state and is bent slightly into the latter. The closing ring can then rotate only so far, in the opening direction, until the securing tongue 26 has reached the edge 23, and is held secure in this position.

In one embodiment of fitting the prosthesis of the present invention, the prosthesis components 1, 2 are first connected to the collarbone and breastbone, respectively, in a known manner, these components being offset in relation to the position aligned on the axis 7, as is shown in FIG. 2 for example. The closing ring 9 is then pushed over the joint head 6, and the slide collar 18 is snapped on. The joint head 6 is then pushed, together with the slide collar 18, right through the opening 20, in the direction of the arrow 28, and into the pot-shaped part 8. By means of axial approximation of the prosthesis parts, the slide collar passes into the recess formed behind the wall part 25. The closing ring 9 is screwed onto the pot-shaped part 8. This is made possible by engaging a tool on the bores 29 distributed about the periphery of the closing ring. Finally, the securing tongue 26 is bent into the securing position in accordance with FIG. 5.

It will be evident that a distraction of the bones to be connected by the prosthesis is needed only for the low height of the wall part 25. This height can be limited to less than 2 mm.

What is claimed is:

1. An endoprosthesis comprising:
    (a) a first prosthetic component comprising a first shaft connected to a pot-shaped part, wherein said pot-shaped part comprises a side opening forming a lateral installation opening; and
    (b) a second prosthetic component comprising;
        i) a second shaft having at one end a joint head, wherein said joint head is dimensioned so that it is laterally insertable into said pot-shaped part through said lateral installation opening, and
        ii) a closing ring, wherein said closing ring slidingly engages said second shaft.

2. The endoprosthesis of claim 1, wherein said second prosthetic component further comprises a slide collar, wherein said slide collar is fitted on said joint head.

3. The endoprosthesis of claim 2, wherein said joint head is inserted into said pot-shaped part.

4. The endoprosthesis of claim 3, wherein said closing ring comprises a flange, wherein said flange secures said slide collar in said pot shaped part.

5. The endoprosthesis of claim 1, wherein said closing ring comprises a cylindrical part.

6. The endoprosthesis of claim 5, wherein said cylindrical part comprises a securing tongue, wherein said securing tongue is formed by two axially parallel incisions in said cylindrical part.

7. The endoprosthesis of claim 6, wherein said joint head is inserted into said pot-shaped part, and said securing tongue is bent into a securing position.

8. The endoprosthesis of claim 1, wherein said closing ring comprises bores distributed about the periphery of said closing ring.

9. The endoprosthesis of claim 8, wherein said joint head is inserted into said pot-shaped part, and said closing ring is secured to said pot shaped part via said bores.

10. An endoprosthesis, comprising a first shaft connected to a joint head via a neck part, a second shaft having a longitudinal axis connected to an enclosure part and a closing part, said enclosure part comprising a neck opening positioned at an axial end of said second shaft and adapted to receive said joint head with pivoting movement, an installation opening for receiving said joint head, edges of said installation opening being offset laterally from said longitudinal axis from said neck opening and a pot-shaped part having a side wall which includes said installation opening, and said closing part being provided to hold said joint head secure within said enclosure part.

11. The endoprosthesis of claim 10, wherein said closing part is a ring threaded to interact with threads on said side wall.

12. The endoprosthesis of claim 10 or 11, further comprising a slide collar disposed between said joint head and said enclosure part and made of a material which promotes sliding between said joint head and said enclosure part.

13. The endoprosthesis of claim 12, wherein said slide collar comprises polyethylene.

14. The endoprosthesis of claim 12, wherein said slide collar forms a closed surface and wherein said installation opening has a width at least as wide as an external diameter of said slide collar.

15. The endoprosthesis of claim 12, wherein said slide collar has a constricted opening portion of a diameter smaller than an outer diameter of said joint head and adapted to allow passage of said joint head by elastic expansion of said slide collar.

16. The endoprosthesis of claim 12, wherein a diameter of a neck opening of said closing part is greater than the diameter of said joint head and smaller than the external diameter of said slide collar.

17. The endoprosthesis of claim 10, wherein said joint head is spherical.

18. The endoprosthesis of claim 12, wherein said joint head is spherical.

19. The endoprosthesis of claim 10, wherein said joint head is surrounded by an elastic sleeve.

20. The endoprosthesis of claim 12, wherein said joint head is surrounded by an elastic sleeve.

* * * * *